(12) United States Patent
Hu et al.

(10) Patent No.: US 7,858,667 B2
(45) Date of Patent: Dec. 28, 2010

(54) ALCOHOL SYNTHESIS FROM CO OR $CO_2$

(75) Inventors: Jianli Hu, Kennewick, WA (US); Robert A. Dagle, Richland, WA (US); Jamelyn D. Holladay, Kennewick, WA (US); Chunshe Cao, Houston, TX (US); Yong Wang, Richland, WA (US); James F. White, Richland, WA (US); Douglas C. Elliott, Richland, WA (US); Don J. Stevens, Richland, WA (US)

(73) Assignee: Battelle Memorial Institute, Richland, WA (US)

( * ) Notice: Subject to any disclaimer, the term of this patent is extended or adjusted under 35 U.S.C. 154(b) by 1046 days.

(21) Appl. No.: 11/611,160

(22) Filed: Dec. 15, 2006

(65) Prior Publication Data

US 2007/0161717 A1 Jul. 12, 2007

Related U.S. Application Data

(60) Provisional application No. 60/751,144, filed on Dec. 16, 2005, provisional application No. 60/823,093, filed on Aug. 21, 2006.

(51) Int. Cl.
*C07C 27/00* (2006.01)

(52) U.S. Cl. .................... 518/715; 518/706; 518/716

(58) Field of Classification Search ................ 518/706, 518/715, 716
See application file for complete search history.

(56) References Cited

U.S. PATENT DOCUMENTS

| 4,119,656 | A | * | 10/1978 | Poutsma et al. ............. 518/715 |
| 4,122,110 | A | | 10/1978 | Sugier et al. |
| 4,831,060 | A | | 5/1989 | Stevens et al. |
| 2003/0185721 | A1 | | 10/2003 | Wang et al. |
| 2004/0223908 | A1 | | 11/2004 | Holladay et al. .......... 423/648.1 |

FOREIGN PATENT DOCUMENTS

| EP | 0034767 | | 2/1981 |
| EP | 0152314 | A2 | 8/1985 |
| EP | 0483919 | A2 | 5/1992 |
| GB | 1296212 | | 11/1972 |

OTHER PUBLICATIONS

Sahibzada et al., methanol synthesis from carbon dioxide/hydrogen over Pd-promoted CuO/ZnO/Al2Oe, (Chemical Abstract 123: 148523 (1995).*
Partial International Search Report for PCT/US2006/047935, mailed May 31, 2007.
Chin et al., "Preparation of a novel structured catalysts bed on aligned carbon nanotube arrays for a microchannel Fischer-Tropsch synthesis reactor," Catal. Today 110 (2005) 47-52.
Extended European Search Report, EP 08009880.9, mailed Oct. 10, 2008.
European Written Opinion, EP 08009880.9, mailed Oct. 10, 2008.
International Search Report for PCT /US2006/047935, mailed Aug. 21, 2007.
Hu et al., (2005) "Conversion of Biomass Syngas to DME Using a Microchannel Reactor"Ind. Eng. Chem. Res. pp. 1722-1727.
Yin et al., (2005) "Characteristics of the Synthesis of Methanol Using Biomass-Derived Syngas" Energy & Fuels 19, pp. 305-310.
Inui et al., (1998) "Effective Synthesus of Ethanol from CO2 on Polyfunctional Composite Catalysts" Catalysis Today 45, pp. 209-214.
Ishiguro et al.,(1998) "Syngas Conversion using Rh VO4 and Rh2MnO4 Catalysts: Regeneration and Redispersion of Rh Metal by Calcination and Reduction Treatments" Catalysis Today 45, pp. 197-201.
Jong et al., (1990) "Highly Dispersed Rh/ SiO2 and Rh/ MnO/SiO2 Catalysts" Journal of Catalysis 124, pp. 520-529.
Elliott et al., (1988) "Mechanism of Ethanol Formation from Syntheses Gas Over CuO/ZnO/Al2O3" Journal of Catalysts 114, pp. 90-99.
Imoto et al., "The Reduction of Zinc Oxide by Hydrogen III. The Effect of Nitrogen on the Reduction," J. Chem. Soc. Japan, pp. 441-444 (1964).
Sahibzada et al., "Hydrogenation of carbon dioxide to methanol over palladium-promoted Cu/ZnO/Al2O3 catalysts," Catal. Today 29 (1996) 367-372.

* cited by examiner

*Primary Examiner*—Jafar Parsa
(74) *Attorney, Agent, or Firm*—Frank Rosenberg; Derek H. Maughan

(57) ABSTRACT

Methods for producing alcohols from CO or $CO_2$ and $H_2$ utilizing a palladium-zinc on alumina catalyst are described. Methods of synthesizing alcohols over various catalysts in microchannels are also described. Ethanol, higher alcohols, and other $C_{2+}$ oxygenates can produced utilizing Rh—Mn or a Fisher-Tropsch catalyst.

32 Claims, 5 Drawing Sheets

US 7,858,667 B2

ALCOHOL SYNTHESIS FROM CO OR $CO_2$

RELATED APPLICATIONS

In accordance with 35 U.S.C. sect. 119(e), this application claims priority to U.S. Provisional Application Nos. 60/751,144 filed 16 Dec. 2005 and 60/823,093 filed 21 Aug. 2006.

GOVERNMENT RIGHTS

A portion of this work was funded by the U.S. Department Energy, Office of Biomass Program, under Contract DE-AC06-76RL01830.

FIELD OF THE INVENTION

The invention relates to methods of alcohol synthesis, catalysts for alcohol synthesis, and systems for synthesizing alcohols. Methods of reacting alcohols are also included in some aspects of the invention.

INTRODUCTION

The Pd/Zn on alumina catalyst is known as a catalyst for the alcohol steam reforming reaction. See, for example, U.S. Published Patent Application 20040223908 and Iwasa et al., "Steam Reforming of Methanol over Pd/ZnO: Effect of the formation of Pd/Zn alloys upon the reaction," Appl. Catal. A: General 125 (1995) 145-147. The mechanism for steam reforming and dehydrogenation of methanol are discussed in Takezawa et al., "Steam Reforming and dehydrogenation of methanol: Difference in the catalytic functions of copper and Group VIII metals," Cat. Today, 36 (1997) 45-56. Although the mechanism for the synthesis of alcohols from CO2 over Pd/Zn is not known, the mechanism over Cu/ZnO is discussed by Fujita et al. in "Mechanisms of Methanol Synthesis from Carbon Dioxide and from Carbon Monoxide at Atmospheric Pressure over Cu/ZnO," J. Catal. 157, 403-413 (1995).

The synthesis of ethanol and higher alcohols from CO2 is possible via the use of composite catalysts that include a Fisher-Tropsch catalyst. Inui and Yamamoto, in "Effective synthesis of ethanol from CO2 on polyfunctional composite catalysts," Catalysis Today vol. 45, pp. 209-214 (1998), reporting using a combination of catalysts, either mixed or in series, to synthesize ethanol and higher alcohols.

SUMMARY OF THE INVENTION

In one aspect, the invention comprises the staged reaction of hydrogen with $C_1^+$ oxygenates to form $C_2^+$ oxygenates. The staging can either be conducted along the length of a microchannel; and/or by reacting $C_1^+$ oxygenates with hydrogen in a first microchannel or first section of microchannel, followed by providing additional hydrogen and again exposing the reaction mixture to reaction conditions in a microchannel. "Reaction conditions" include the presence of a catalyst at a suitable temperature. In some preferred embodiments, the reaction involves the staged addition of hydrogen to a feed stream comprising CO. As alternatives to staging hydrogen, CO and/or $CO_2$ can be added in a stagewise fashion, likewise $C_1^+$ oxygenates can be added in a staged fashion; furthermore, mixtures of these, such as a mixture of $H_2$ and $CO_2$ can be added in a stagewise fashion to a microchannel reaction channel (also called microchannel reaction chamber). In preferred embodiments, the microchannel reaction chamber comprises an alcohol synthesis catalyst as described herein. Microchannel apparatus for staging other reactions is known and such apparatus can be adapted for the inventive processes. For example see, U.S. Published Patent Application 2006/0129015 by Tonkovich et al. (synthesis of hydrogen peroxide) and U.S. Pat. No. 7,442,360 also by Tonkovich et al; which are both incorporated herein.

In another aspect, the invention provides a method of synthesizing alcohols comprising: contacting hydrogen and CO over an alcohol catalyst in a microchannel. This method is further characterized by any of the results described herein. For example, at CO conversions of at least 20%, the method surprisingly results in a selectivity to $C_2^+$ oxygenates (preferably selectivity to ethanol) of at least 30%, more preferably at least 40%, and still more preferably at least 50%, and in some embodiments a selectivity of 40 to about 60%, in some embodiments up to about 56%. This can be compared with a selectivity reported in the literature of only 20%. Preferably, the process is conducted at a relatively high throughput, such as a GHSV of at least 1000 $h^{-1}$, more preferably at least 3000 $h^{-1}$, in some embodiments 2000 to 100,000 $h^{-1}$, in some embodiments 2000 to about 4000 $h^{-1}$. The use of a microchannel reactor enables highly exothermic CO hydrogenation reaction to be operated in an isothermal mode to achieve high productivity. Integration of a catalyst in a microchannel reactor allows hydrogenation to alcohols at high throughput and high space time product yield and surprisingly increased product selectivity. Heat flux from the reaction microchannel is preferably at least 5 W/cc, and in some embodiments is in the range of 5 to 8 W/cc, where the "cc" volume is the volume of the reaction chamber (i.e., the portion of the microchannel where catalyst is present in either a flow-by or flow through configuration. The catalyst may further include a Fisher-Tropsch catalyst to increase production of ethanol and higher alcohols.

In another aspect, the invention provides a method of synthesizing alcohols from CO comprising: flowing a reactant gas mixture comprising CO and $H_2$ into contact with a catalyst; wherein the catalyst comprises Pd and Zn dispersed on alumina; and forming an alcohol or alcohols. In some embodiments, the alcohol or alcohols formed in the step of forming an alcohol or alcohols consists essentially of methanol. The catalyst may further include a Fisher-Tropsch catalyst making it possible for the alcohol or alcohols to contain substantial amounts of ethanol and higher alcohols.

In a further aspect, the invention provides a new method of synthesizing alcohols from $CO_2$ comprising: flowing a reactant gas mixture comprising $CO_2$ and $H_2$ into contact with a catalyst; wherein the catalyst comprises Pd and Zn dispersed on alumina; and forming an alcohol or alcohols.

In a related aspect, the invention provides a method of synthesizing ethanol and higher alcohols from $CO_2$ comprising: flowing a reactant gas mixture comprising $CO_2$ and $H_2$ into contact with a catalyst; wherein the catalyst comprises: (a) Pd—Zn alloy dispersed on alumina and (b) a Fisher-Tropsch catalyst; and forming ethanol and higher alcohols.

In another aspect, the invention provides a method of synthesizing $C_2^+$ oxygenates comprising: a first step of subjecting a Rh- or Pd-containing composition to a RedOx treatment to form a catalyst; then, in a subsequent step, contacting a $C_1^+$ oxygenate with hydrogen in the presence of the catalyst to form a $C_2^+$ oxygenate. The step of contacting a $CO_1^+$ oxygenate with hydrogen in the presence of the catalyst is preferably conducted in a microchannel. Rh catalysts are preferred because of their greater selectivity. Rh on silica is particularly preferred. A RedOx treatment comprises a first step of reducing the Rh-containing (or, less preferably, the Pd-containing) composition at elevated temperature. Reduction is preferably carried out in the presence of hydrogen. A RedOx treatment further comprises a subsequent, second step of oxidation at elevated temperature. Elevated temperature is above room temperature, preferably at least 100° C., more preferably at least 200. In some embodiments, reduction is carried out at a higher temperature than oxidation. In some embodiments, reduction is carried out in the temperature range of 300 to 400° C. In some embodiments, oxidation is carried out in the temperature range of 200 to 300° C. A cycle has a reduction step and an oxidation step, and a RedOx treatment comprises at least one cycle, preferably at least 2 cycles. For catalyst systems comprising Rh and/or Pd, such as a hybrid catalyst system consisting of CuZnAl and Rh—Mn/$SiO_2$, it has been surprisingly discovered that a RedOx treatment can enhance overall CO conversion while maintaining or increasing product selectivity.

In another aspect, the invention provides a method of synthesizing alcohols comprising: contacting hydrogen and CO over an alcohol catalyst in a microchannel at high temperatures. In this case, "high temperatures" are temperatures significantly higher than reported in the prior art. For example, for the reaction catalyzed over a Cu catalyst, the invention is conducted at a temperature of at least 250 C, in some embodiments at least 270 C, while the literature reports that Cu catalysts should not exceed 230 C. Similarly, in this inventive method, the reaction over a Rh on silica catalyst can be conducted at a temperature of at least 300 C, in some embodiments at least 320 C.

In another aspect, the invention comprises the reaction of hydrogen with $C_1^+$ oxygenates over a thin layer catalyst to form $C_2^+$ oxygenates. Preferably, the reaction is carried out in a microchannel. A thin layer of catalytically active material can be applied directly to a reaction chamber (preferably a microchannel) wall, or onto a catalyst insert that is inserted into a reaction chamber (preferably a microchannel reaction chamber). A thin layer is preferably 100 μm or less, more preferably 50 μm or less, in some embodiments 30 μm or less, in some embodiments 20 μm or less, in some embodiments 10 μm or less, and in some embodiments 5 μm to 50 μm.

The invention also includes combinations of these methods. For example, enhanced ethanol selectivity can be obtained by reaction in a microchannel over a thin layer of catalyst; preferably conducted in conjunction with hydrogen staging. Hydrogen staging keeps a desirable ratio of reactants to hydrogen throughout the reaction.

In several aspects, the invention is described as methods of conducting reactions. These methods may alternatively be described as "systems," and the invention also includes systems comprising any of the methods described herein. Systems of the invention can be described as including apparatus and/or catalyst in combination with reactants and/or products. Optionally, systems can be further characterized by the conditions at which they operate.

Various embodiments of the invention can provide numerous advantages including one or more of the following: high carbon monoxide or carbon dioxide conversions, high alcohol selectivity, low methanol or methane selectivity, operation at short contact times, able to operate at higher temperatures than conventional systems such as the CuZnAl catalyst—which enables a larger throughput due to the enhanced rate of reaction at high temperatures, non-pyrophoric nature of catalyst, and high stability over time even under relatively high temperatures.

Glossary

An "alcohol catalyst" is a composition that catalyzes the reaction of hydrogen with $C_1^+$ oxygenates. There are numerous compositions known to be alcohol catalysts. Preferred alcohol catalysts include Rh, preferably Rh on silica, in some embodiments Rh disposed on zirconia and/or magnesia, molybdenum sulfide, preferably doped with K and in some embodiments mixed with Co; Pd/Zn; and Cu, preferred copper catalyst formulations include $Cu/ZnO/Cr_2O_3$—Cs and Cu—CoO—$ZrO_2$—K; and hybrid catalysts such as a mixture containing Cu and Rh.

For purposes of the present invention, $C_1^+$ oxygenates are defined as CO, $CO_2$, methanol ($CH_3OH$), or formaldehyde ($CH_2O$) and mixtures thereof. In its broader aspects, the invention comprises the use of a feed stream comprising $C_1^+$ oxygenates. In some preferred embodiments, the feed stream (reactant) comprises CO. Hydrogen (H2) may be present in a feed stream or may be added during processing.

For purposes of the present invention, $C_2^+$ oxygenates are defined as those compounds comprising at least 2 carbon atoms and one oxygen atom. This definition is for the chemist of ordinary skill that would understand the range of compounds that could reasonably be expected to form in the types of processes described herein (that is, from the catalytic reaction of $C_1^+$ oxygenates). In some preferred embodiments, the desired product may be limited to ethanol and higher alcohols. In some embodiments, the synthesis of ethanol is especially preferred.

As is conventional patent terminology, "comprising" means including and when this term is used the invention can, in some narrower preferred embodiments, be described as "consisting essentially of" or in the narrowest embodiments as "consisting of." Aspects of the invention described as "comprising a" are not intended to be limited to a single component, but may contain additional components. Compositions "consisting essentially of" a set of components allow other components that so not substantially affect the character of the invention, and, similarly, compositions that are "essentially" without a specified element do not contain amounts of the element as would substantially affect the desired properties.

Gas hourly space velocity ("GHSV") is defined as total hourly flow rate (L/h) at standard conditions (0° C. at 1 atm) divided by reaction zone volume (L). In the case of packed bed reactor using powdered catalyst, the reaction zone volume equals the catalyst volume. In a microchannel reactor, the reaction zone also includes the volume of a bulk flow path past a catalyst—in other words, it is the volume of the microchannel where catalyst is present within the cross-sectional area perpendicular to flow (for example, it includes the volume above a wall coating).

A "microchannel" is a channel having at least one internal dimension (wall-to-wall, not counting catalyst) of 1 cm or less, preferably 2 mm or less (in some embodiments about 1.0 mm or less) and greater than 100 nm (preferably greater than 1 μm), and in some embodiments 50 to 500 μm. Microchannels are also defined by the presence of at least one inlet that is distinct from at least one outlet. Microchannels are not merely channels through zeolites or mesoporous materials. The length of a microchannel corresponds to the direction of flow through the microchannel. Microchannel height and width are substantially perpendicular to the direction of flow of through the channel. In the case of a laminated device where a microchannel has two major surfaces (for example, surfaces formed by stacked and bonded sheets), the height is the distance from major surface to major surface and width is perpendicular to height.

In some preferred embodiments, microchannel reactors are used that include a plurality of microchannel reaction channels, preferably in thermal contact with a plurality of adjacent heat exchange microchannels. A plurality of microchannels may contain, for example, 2, 10, 100, 1000 or more channels. In preferred embodiments, the microchannels are arranged in parallel arrays of planar microchannels, for example, at least 3 arrays of planar microchannels. In some preferred embodiments, multiple microchannel inlets are connected to a common header and/or multiple microchannel outlets are connected to a common footer. During operation, interleaved heat exchange layers (if present) contain heating and/or cooling fluids flowing in microchannels. Non-limiting examples of this type of known reactor usable in the present invention include those of the microcomponent sheet architecture variety (for example, a laminate with microchannels) exemplified in U.S. Pat. Nos. 6,200,536 and 6,219,973 (both of which are hereby incorporated by reference). Performance advantages in the use of this type of architecture include their relatively large heat and mass transfer rates. Microchannel reactors can combine the benefits of good heat and mass transfer, excellent control of temperature, residence time and minimization of by-products. Pressure drops can be low, allowing high throughput. Furthermore, use of microchannel reactors can achieve better temperature control, and maintain a relatively more isothermal profile, compared to conventional systems. In addition to the process microchannel(s) additional features such as microchannel or non-microchannel heat exchangers may be present. Microchannel heat exchangers are preferred. Heat exchange fluids may flow through adjacent heat transfer microchannels, and can be gases or liquids and may include steam, liquid metals, or any other known heat exchange fluids—the system can be optimized to have a phase change in the heat exchanger. In some preferred embodiments, multiple heat exchange layers are interleaved with multiple reaction microchannels (for example, at least 10 heat exchanger layers interleaved with at least 10 process microchannel layers. Microchannels are defined by microchannel walls.

DETAILED DESCRIPTION OF THE INVENTION

Figure 1:
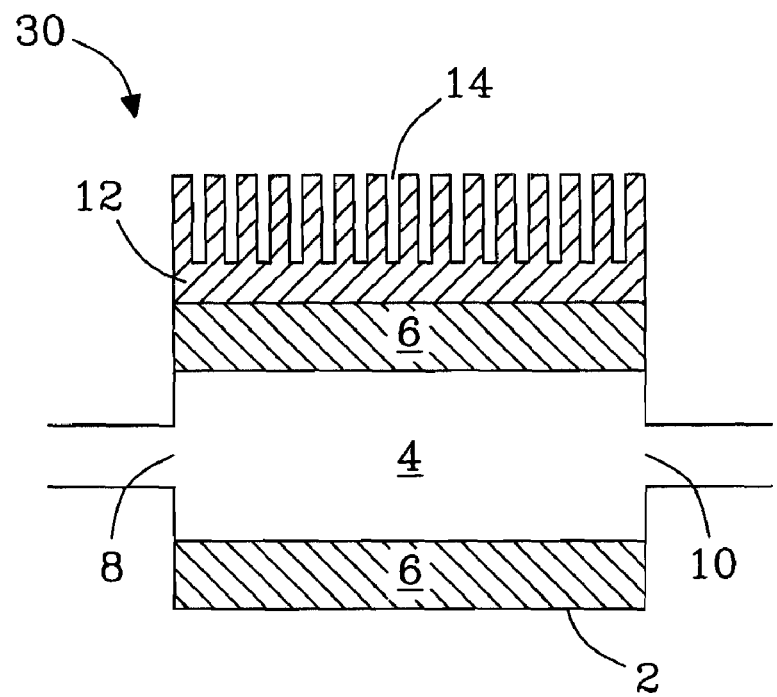
FIG. 1 is a schematic of a reactor that includes a cross-sectional view of a water gas shift reactor that includes a microchannel heat exchanger.

In some catalysts of the present invention, a Pd—Zn alloy is dispersed on an alumina support. Alumina is a particularly desirable support because of its low cost, high surface area, and good interaction with Pd/Zn. In some preferred embodiments, the catalyst contains 2 to 10 weight % Pd (including the weight of the alumina, upon which the Pd/Zn is dispersed, but not including any underlying material such as a metal felt or foam), and in some embodiments 5 to 10 wt %. In some preferred embodiments, the alcohol synthesis catalyst has a Pd:Zn molar ratio of 0.1 to 0.5, more preferably 0.2 to 0.45, and still more preferably 0.25 to 0.39. Preferably, there is essentially no unalloyed Pd, which can reduce alcohol yields. In some preferred embodiments, a Pd/Zn catalyst is prepared by co-precipitating Pd and Zn; these components may be coprecipitated using inorganic or organometallic precursors. Prior to operation, the steam reforming catalyst may advantageously be subjected to an activation treatment, preferably reduction at 350-500° C. A Pd—Zn catalyst is superior to a Pd catalyst; in some embodiments, crystalline ZnO is present in the catalyst. A similar catalyst is described in published U.S. patent application 200400223908A1 for catalyzing alcohol steam reforming.

In some preferred catalysts, Rh and Mn are dispersed on a silica, titania, or zirconia support. In preferred embodiments, Rh is present at 1 wt % to 10 wt %, more preferably 4-6%. Mn is preferably in the range of 1 to 6 wt %, most preferably 3-4%. In some preferred embodiments, the catalyst consists essentially of Rh, Mn and silica.

The catalyst may take any conventional form such as a powder, pellet, washcoat, etc. Preferably, the catalyst is immobilized rather than flowing or fluidized catalyst. Additionally, in some preferred configurations, the catalyst includes an underlying large pore support. Examples of preferred large pore supports include commercially available metal foams and, more preferably, metal felts. Prior to depositing the Pd—Zn on alumina catalyst, the large pore support has a porosity of at least 5%, more preferably 30 to 99%, and still more preferably 70 to 98%. Preferably, the support has an average pore size (sum of pore diameters/number of pores) of from 1 μm to 1000 μm as measured by optical and scanning electron microscopy. Preferred forms of porous supports are foams and felts. Foams are continuous structures with continuous walls defining pores throughout the structure. Felts are fibers with interstitial spaces between fibers and includes tangled strands like steel wool. Another support can be a monolith, such as a honeycomb. Also, the catalyst can be dispersed on the walls of a channel or array of microchannels (channels having a dimension of 5 mm or less) in a microreactor. Various supports and support configurations are described in U.S. Pat. No. 6,680,044, which is incorporated by reference. U.S. Pat. No. 6,488,838 (filed Aug. 17, 1999) is also incorporated herein.

Catalysts of the present invention may be used in conjunction with a large pore support. A catalyst with a large pore support (and including a catalytically active metal) preferably has a pore volume of 5 to 98%, more preferably 30 to 95% of the total porous material's volume. Preferably, at least 20% (more preferably at least 50%) of the material's pore volume is composed of pores in the size (diameter) range of 0.1 to 300 microns, more preferably 0.3 to 200 microns, and still more preferably 1 to 100 microns. Pore volume and pore size distribution are measured by mercury porisimetry (assuming cylindrical geometry of the pores) and nitrogen adsorption. As is known, mercury porisimetry and nitrogen adsorption are complementary techniques with mercury porisimetry being more accurate for measuring large pore sizes (larger than 30 nm) and nitrogen adsorption more accurate for small pores (less than 50 nm). Pore sizes in the range of about 0.1 to 300 microns enable molecules to diffuse molecularly through the materials under most gas phase catalysis conditions.

For the formation of ethanol and higher alcohols, a Fisher-Tropsch catalyst can be used in combination with a catalyst for alcohol synthesis, for example the Pd—Zn alloy or a conventional Cu/Zn/Al catalyst and a Fisher-Tropsch catalyst. Conventional Fischer-Tropsch catalsyts are based on iron (Fe), cobalt (Co), nickel (Ni), ruthenium (Ru), rhenium (Re), osmium (Os) and combinations thereof; and any of these may be employed in the present invention. In addition to these catalyst metals, a promoter may be added. Promoters could include transition metals and metal oxides, lanthanide metals or metal oxides, and group IA elements (except H). As is known, the Fisher-Tropsch metal and optional promoters can be dispersed on a support material (such as alumina) and may further include an underlying support (such as a metal felt).

Certain aspects of the catalyst may be best characterized with reference to measurable properties of the alcohol synthesis reaction. In some preferred embodiments, when the catalyst is tested by placement in a reaction chamber (as described in the examples) and contacted with a reactant gas mixture and other conditions as described in the examples, the catalyst can be defined by the measured properties—for example, properties that are within about 10% (or about 5%) of any selected measurement in the examples; or properties that at least a certain level shown in the examples, or within a range shown in the examples, or having a stability as shown in the examples. For one example, a catalyst can be defined by alcohol productivities that are within about 10% (or about 5%) of the productivities described in the examples (when the catalyst is catalyst is tested according to the procedures set forth in the examples). In this case, it can be said that the catalyst is "characterizable" by a given property when tested under a specified set of conditions (which may be taken from the examples). Methods may also be characterized by the values shown in the examples.

In some inventive methods of synthesizing alcohols, a reactant gas mixture comprising carbon monoxide (or carbon dioxide, or a mixture of CO and CO2) and hydrogen is contacted with an alcohol synthesis catalyst. Inert gases such as nitrogen may also be present. In certain preferred embodiments, the gas mixture comprises, in mole % (which is equivalent to partial pressures) a ratio of (CO+CO2):$H_2$ of 1:1.5 to 1:4 more preferably 1:2 to 1:3. Where the reactant gas consists essentially of CO and hydrogen, the ratio is preferably 1:1.5 to 1:3 and where the reactant gas consists essentially of $CO_2$ and hydrogen, the ratio is preferably 1:2 to 1:4. In the case of methanol synthesis, the temperature at the catalyst during the reaction is preferably less than 500° C., more preferably in the range of 220 to 450° C.; in some embodiments 280° C. or above, in some embodiments 350° C. or above; and preferably the catalyzed reaction runs without a significant change (less than about 5%) of a measured property for at least 20 hours, more preferably at least 10 days. A stable reaction runs at essentially the same productivity. For methanol, minimum productivity should be at least 400 g/hr/L cat. Likewise, when the Pd—Zn catalyst is mixed with an FT catalyst, the temperature is preferably less than 500° C., more preferably in the range of 280 to 450° C.; still more preferably in the range of 350 to 400° C.; and preferably the catalyzed reaction runs stably for at least 20 hours, more preferably at least 10 days. For ethanol, minimum productivity should be at least 200 g/hr/L cat. When an alcohol synthesis catalyst and an FT catalyst are used in series, the FT reaction is desirably conducted at a higher temperature and higher pressure than the reaction over the alcohol synthesis catalyst. For the FT zone, the temperature has the preferred temperature ranges described above for ethanol; for a Pd—Zn zone, preferably 280-330° C., and in some embodiments in the range of 290 to 310° C. The pressure is preferably at least 1 MPa, more preferably at least 5 MPa, and in some embodiments in the range of 1 to 30 MPa, in some embodiments 2-15 MPa, and in some embodiments 3-10 MPa. Flow rates (GHSV) through the reaction channels is preferably at least 1000 $hr^{-1}$, more preferably at least 10,000 $hr^{-1}$, in some embodiments 10,000-360,000 $hr^{-1}$, in some embodiments 25,000-100,000 $hr^{-1}$, in some embodiments 25,000-81,000 $hr^{-1}$, and in some embodiments 25,000-50,000 $hr^{-1}$. Shorter contact times (defined as the total volume of catalyst-containing reaction chambers divided by the total volume of reactant gases corrected to 273K and 1 atm, and assuming ideal gas behavior) are preferred to minimize reactor volume, and are preferably less than 0.4 s, more preferably in the range of 10 to 140 ms. Conversion of carbon monoxide (defined as CO mole change between reactant and product divided by moles CO in reactant) or carbon dioxide, typically measured in conjunction with the above-described ranges, is preferably at least 50%; and in some preferred embodiments conversion is in the range of 10 to 80%. Selectivity to methanol is preferably at least 80%, more preferably at least 90%.

For ethanol synthesis over a catalyst comprising Rh and Mn, the following ranges may be preferred:

T=240-340° C. (preferred at 260-280° C.)

P=10-100 atm (preferred >50 atm)

GHSV=1000-100,000 $h^{-1}$ (more preferred at least 2000; in some embodiments 2000-10,000 $h^{-1}$)

Conversion of $CO_2$=20-80% (in some embodiments, 40-50%)

Selectivity to Ethanol=20-80% (in some embodiments, 40-60%)

For ethanol synthesis over a catalyst comprising a conventional Cu/Zn/Al catalyst in combination with an FT catalyst, the following ranges may be preferred:

T=240-420° C. (preferred at 280-370° C.)

P=10-120 atm (preferred >50 atm)

GHSV=1,000-100,000 $h^{-1}$ (preferred 20,000-50,000 $h^{-1}$)

Conversion of $CO_2$=20-80% (in some embodiments, 40-50%)

Selectivity to Ethanol=10-60% (in some embodiments, 20-40%)

The alcohol forming reaction can occur in a single step or in multiple steps. In one embodiment, the method has a first step of a relatively low temperature methanol synthesis over a Pd—Zn catalyst followed by a second, higher temperature step over a Fisher-Tropsch catalyst such as a Fe-based catalyst. The temperature difference (based on average temperature of each step) could be at least 20° C. (or at least 40° C.). This multistep reaction could be conducted in separate reactors or in a single reactor having multiple zones, such as a first relatively cool reaction zone followed by a hotter FT reaction zone.

In preferred embodiments, the temperature of a step, for example, alcohol synthesis or Fischer-Tropsch reaction is carried out isothermally in a microchannel. In preferred embodiments, temperature variation over the length of a catalyst is 10° C. or less, more preferably 5° C. or less, and still more preferably 2° C. or less.

Alcohols or other $C_{2+}$ oxygenates made in any of the inventive processes can be converted to unsaturated compounds, for example, by a dehydration reaction. For example, ethanol can be dehydrated to form ethene over alumina or a zeolite (such as ZSM-5) at, preferably, 200-300 C (more preferably 260-280 C), preferably at a pressure of about 1 to about 5 atm, preferably at a GHSV=1000-100,000 h$^{-1}$ (preferably 2000-10,000 h$^{-1}$), with preferably an ethanol conversion of at least 90% and a preferred selectivity to ethene of 95% or more. Another alternative is a hydrodeoxygenation (HDO) reaction in which H$_2$ reacts with a C$_{2+}$ oxygenate to form water and an unsaturated compound; preferred conditions include a NiMo or CoMo catalyst, pressure of about 1 to 20 atm, temp 240 to 330 C, GHSV=1000-100,000 h$^{-1}$, with preferably an ethanol conversion of at least 90% and a preferred selectivity to ethene of 95% or more. In some preferred embodiments, the reactions occur within the same microchannel, either in the same area or in sequential areas of the microchannel, and in some preferred embodiments without any intervening steps such as separation steps.

As discussed in published U.S. patent application 200400223908A1, a Pd—Zn alloy catalyst can be made by a process that includes the steps of: providing an alumina support; adding a solution comprising dissolved zinc to the solid metal oxide support; adding a base to increase pH; and subsequent to at least a portion of the step of adding a base, depositing Pd. The alumina support could itself be deposited (either before or after the other steps) onto a large pore support. This method is especially advantageous in aqueous solutions where the metal oxide support would normally have an acidic surface. The dissolved Zn is at least partially, and more preferably completely, dissolved in a solvent. The solution containing dissolved zinc contains at least zinc, but may also contain other components including metals; in some preferred embodiments there are no other metals in the zinc solution; in some preferred embodiments the solution is 0.1 to 3 M zinc. The order of addition, alumina to Zn solution or Zn solution to alumina is not critical and the inventive method includes either order. The base can be added before, during or after the zinc solution is added. Preferably, the base is added after the zinc solution, more preferably it is added to slowly to result in gradual precipitation of zinc. Preferably, the base is an aqueous ammonia solution. In some preferred embodiments, base is added until a pH of 7 or greater is obtained. Improvement is obtained where Pd is added after at least a portion of the base is added. Preferably, Pd is added after all the base has been added—this results in the greatest percentage of Pd being disposed on the catalyst surface. Pd is preferably deposited on the catalyst after deposition of the zinc, and, in some preferred embodiments, after the zinc-containing layer has been dried and, optionally, calcined. In some preferred embodiments, Pd is impregnated onto the Zn-containing support in solution, preferably aqueous solution.

Alternatively, the catalyst can be made by the incipient wetness impregnation technique by impregnating alumina with a solution of Pd and Zn. The resulting material is then dried and calcined, preferably in the range of 350 to 450° C.

The catalyst should be reduced to form a Pd—Zn alloy. In some preferred embodiments, the catalyst is reduced in the presence of H$_2$ at a temperature of at least 350° C., in some embodiments above 400° C., and in some embodiments in the range of 400 to 500° C. In some preferred embodiments, the catalyst is prepared and reduced under hydrogen with temperatures never exceeding 400° C. preferably, calcining of the Zn-containing catalyst, either before and/or after depositing Pd, is conducted at 200 to 400° C., more preferably 250 to 350° C. Similar temperature ranges can be used when reducing (and operating) the catalyst. The low temperature treatment increases catalyst life and surface area.

The invention also includes catalysts made by the foregoing methods.

One embodiment of a reactor 2 is shown in cross-section in FIG. 1. The reaction chamber 4 contains catalyst 6 and has an inlet 8 and outlet 10. In FIG. 1, the catalyst is shown on the top and bottom of the reaction chamber with an open channel from the reactor inlet to the outlet—this configuration is called "flow-by." Other configurations, such as "flow-through" where flow is directed through a porous catalyst, are, of course, possible. To improve heat transfer, a microchannel heat exchanger 12 can be placed in contact with the reaction chamber. The microchannel heat exchanger 12 has channels 14 for passage of a heat exchange fluid. These channels 14 have at least one dimension that is less than 1 cm, preferably less than 1 mm. The distance from the channels 14 to catalyst 6 is preferably minimized in order to reduce the heat transport distance. Microchannel heat exchangers can be made by known techniques such as electrodischarge machining (EDM).

Figure 2:
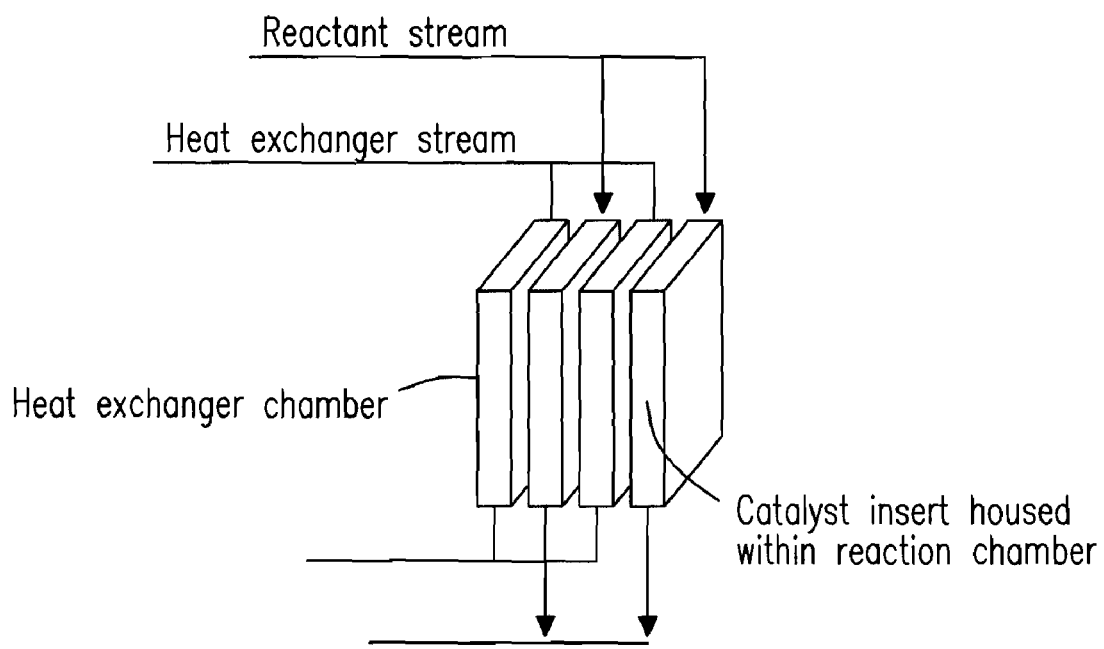
FIG. 2 is a schematic view of an interleaved microchannel reactor oriented in a co-current flow configuration.

The preferred reaction chamber for the alcohol synthesis reaction may be of any length or height. The preferred reaction chamber width is 5 mm or less, more preferably 2 mm or less, and in some embodiments, the reaction chamber width is 1 mm or less. The reaction chamber is preferably in thermal contact with a heat exchange chamber to remove the exothermic reaction heat. The heat exchange chamber in thermal contact with the reaction chamber may also be of any length or height. Preferably the length and height of the heat exchange chamber is close to the dimensions of the reaction chamber. Most preferably the heat exchange chamber is adjacent to the reaction chamber in an interleaved chamber orientation (see FIG. 2—width is the direction in which the interleaved reaction chambers and heat exchange chambers stack) in which there are at least three reaction channels (in this embodiment, the terms channels and chambers are used interchangeably) interleaved with at least three heat exchange channels. The width of the heat exchanger chamber preferably is 5 mm or less, more preferably 2 mm or less, and in some embodiments, the heat exchange chamber width is 1 mm or less. The direction of flow in the heat exchange chamber may be either co-current, counter-current, or cross-flow. The short distances for mass and heat transfer in a microchannel apparatus will enable excellent performance.

The reactor may also be configured by placing the reaction chamber adjacent to a heat exchanger chamber that is comprised of an array of microchannels rather than a single microchannel. In this configuration the width of the reaction chamber may exceed 5 mm, but at least one dimension of a single microchannel in the array is preferably less than 5 mm. Preferably this dimension is less than 2 mm. The desired width of the reaction chamber can be a strong function of the effective thermal conductivity of the catalyst. The higher the effective thermal conductivity of the catalyst, the wider can be the catalyst and still enable rapid heat removal. There are by now numerous microchannel reactor designs known in the literature, and the skilled worker can select an appropriate design for conducting the alcohol synthesis reaction in microchannel apparatus.

EXAMPLES

The following examples are descriptions based on typical conditions used to make numerous samples. Certain temperatures, etc. set forth preferred values for conducting various steps.

Al$_2$O$_3$ supported Pd—Zn catalysts were prepared using a one-step co-impregnation method. Specifically, a concentrated palladium nitrate solution (20.19 wt % Pd, Engelhard Corp.) was mixed with $Zn(NO_3)_2 \cdot 6H_2O$ (99.5%, Aldrich) at 60° C. A neutral $\gamma$-$Al_2O_3$ support (Engelhard Corp.) with a BET surface area of 230 $m^2$/g, and 70-100 mesh particle size, was pre-calcined at 500° C. for 2 hrs and kept at 110° C. prior to the incipient-wetness impregnation step. The support was impregnated at 60° C. with appropriate amount of the pre-mixed Pd and Zn nitrate solution to obtain the final products with various Pd loadings (in this case 8.9%) and Pd/Zn molar ratios (in this case 0.38). The wet sample was kept at 60° C. for 1 hour before drying in air at 110° C. overnight. The dried sample was then calcined at 350° C. for 3 hours.

In methanol synthesis, Pd/ZnO—$Al_2O_3$ catalyst was used alone. However, in ethanol and $C_2^+$ alcohol synthesis, Pd/ZnO—$Al_2O_3$ catalyst was combined with FeCuAlK (Fe:Cu:Al:K=1:0.03:2:0.7) catalyst known as a C—C chain propagation catalyst (F-T catalyst). The latter catalyst was prepared by co-precipitation from their corresponding nitrate salts. During activity testing, the above-mentioned two catalysts were combined by physically mixing their powders, then using a tablet machine to make then into a size of 10 mm in diameter and 2 mm in height. The tablets were crushed and sieved to a range of 70-100 mesh. The experiments were carried out in a fixed-bed reactor made of 316 stainless steel tube with diameter of 4 mm. The reactor was configured for high pressure down flow operational mode. To minimize methanation reaction in the stainless steel reactor, silica ($SiO_2$) coated stainless steel tubing was used in the high-temperature preheating zone. All the experiments were carried out under isothermal conditions as indicated by the uniform temperature distribution along catalyst bed. Catalyst was reduced in situ in 10% hydrogen at 400° C. and ambient pressure. After reduction, a mixture of $N_2$/$H_2$ was fed during startup to establish steady-state flow and to heat the reactor to the desired temperature. When the catalyst bed temperature reached the target, premixed $CO_2$/$H_2$ at the desired ratio was fed into the reactor. Experiments were conducted at temperatures from 260-400° C., pressure from 2-8.1 MPa and GHSV from 25000-81000 $h^{-1}$. The typical feed composition was $CO_2$:$H_2$=1:3. For each run using powdered catalyst, 0.20 grams of catalyst were loaded into the reactor, and the volume is measured. Total feed flow rate was set to achieve the desired gas hourly space velocity (GHSV), which is measure by reactor channel volume. The gaseous products were analyzed by on-line gas chromatography (HP 5890 GC) equipped with both TCD and FID detectors. Liquid products were collected in a cold trap at −3° C. and were analyzed by both GC-mass spectrometry and GC. Carbon dioxide conversion and product selectivity were calculated based on feed and product flow rates and carbon balance.

Methods of Catalyst Preparation and Activation of Rh—Mn Containing Catalysts $SiO_2$ was supplied by Davison, which had been pre-calcined in air at 550° C. (BET surface area=400 $m^2$/g). A rhodium nitrate solution containing 10% Rh metal purchased from Engelhard was used as precursor. Although Rh/$SiO_2$ itself can catalyze syngas conversion to ethanol, the use of appropriate promoters (e.g. Mn, V, etc.) improves activity and selectivity to ethanol. $Mn(NO_3)_2$ (99%) and $NH_4VO_3$ (>98%) were obtained from Aldrich and used as precursors for Mn and V, respectively. Rh—Mn/$SiO_2$ catalyst was prepared by co-impregnating Rh and Mn precursors on $SiO_2$ support using incipient wetness technique. Final concentration of Rh and Mn were controlled at level of 6 wt % and 1.5 wt %, respectively. After impregnation, all catalysts were subject to air calcination at 350° C. for 3 hours. A methanol synthesis catalyst, F51-8PPT (Katalco Corporation) was modified by impregnating 3% Cs using incipient wetness technique. This catalyst was used as a comparison higher alcohol synthesis catalyst. Catalysts were tested in both powdered form and structured monolith type configuration. When tested in the powder form, fine particle powder catalysts were pelletized, crushed and sieved into 70-100 mesh before placed into microchannel reactor. The purpose was to minimize pressure drop. Structured Rh—Mn/$SiO_2$ catalyst was prepared by wash coating technique. Powdered Rh—Mn/$SiO_2$ catalyst was ball-milled with water as a medium for 24 hours, after which the ball-milled catalyst slurry was wash coated on FeCrAlY metallic felt. Characterization by SEM showed that the catalyst particle size on the structured catalyst varied between 0.5-2 micron. After wash-coating to desired weight gain, the felt catalyst (structured catalyst) was installed into a microchannel reactor equipped with active cooling functions.

The catalysts were reduced with flowing 10% hydrogen in Helium in the 220-350° C. temperature range under atmospheric pressure. A special catalyst treatment procedure was developed where catalysts were treated by reduction-oxidation cycles (RedOx). During the RedOx treatment, catalyst is reduced first by 10% hydrogen at 350° C. for 12 hours, then cooled to room temperature. After reactor was purged by nitrogen, 2% oxygen in Helium was introduced and reactor temperature was increased to 250° C. at ramping rate of 1° C./minute. The duration of oxidation is 2 hours, after which the reactor was cooled to room temperature under Helium gas flow. The above reduction and oxidation procedure was repeated once, and the catalyst was finally reduced by 10% hydrogen in Helium before feed gas mixture was introduced.

Microchannel Reactor and Operation

The experiments were carried out in a microchannel reactor (316 stainless steel), with the channel dimensions of 5.08 cm×0.94 cm×0.15 cm. The microchannel reactor was configured for high pressure down flow mode. The schematic diagram of the reactor system and microchannel reactor assembly were similar to those described in reference 12. To minimize methanation reaction in the stainless steel reactor, silica ($SiO_2$) coated stainless steel tubing was used in the high-temperature preheating zone. Experiments were conducted at temperatures from 260-300° C. and pressure from 2-5.4 MPa. All the experiments were carried out under isothermal conditions as indicated by the uniform temperature distribution along the catalyst bed.

A mixture of $N_2$/$H_2$ was fed during startup to establish steady-state flow and to heat the reactor to the desired temperature. When the catalyst bed temperature reached the target, premixed syngas at the desired ratio was fed into the reactor. The typical feed composition was CO:$H_2$:$CO_2$:Ar=30:62:4:4. The presence of Ar served as the internal standard for conversion and selectivity calculation purposes. Total feed flow rate was set to achieve the desired gas hourly space velocity (GHSV). The reaction products were analyzed by on-line gas chromatography (HP 5890 GC) equipped with both TCD and FID detectors. GC column used is GS-Q 30 m manufactured by JW Scientific. Temperature program of 5° C./min to 300° C. was chosen for the analysis. Liquid products were collected in a cold trap at −3° C. and were also analyzed by GC-mass spectrometry. Carbon monoxide conversion and product selectivity were calculated based on feed and product flow rates and carbon balance.

Effect of Reaction Temperature and Pressure on Performance of Rh—Mn/$SiO_2$ Catalyst The influence of reaction temperature, pressure and feed compositions on catalytic activity of Rh—Mn/$SiO_2$ catalyst is depicted in Tables 1 and 2. Major products were comprised of methane, $CO_2$, MeOH, EtOH, and $C_2^+$ hydrocarbons and oxygenates. To study the effect of temperature, the reactor was operated in an isothermal mode. Multiple thermocouples were installed in the catalyst bed and the furnace temperature was adjusted to control catalyst bed temperature. The temperature difference between the top and bottom of the catalyst bed was measured to be within ±2° C., indicating excellent heat removal capability of the microchannel reactor. As illustrated in Table 1, on raising catalyst temperature from 280 to 300° C., CO conversion increases with increasing temperature (Conditions 1&2). However, methane selectivity increases from 38.4% to 48.1%, and meanwhile, selectivity to ethanol decreases remarkably. This suggests that alcohol synthesis over Rh—Mn/$SiO_2$ is preferred to be operated at temperatures lower than 280° C. To further illustrate the temperature effect, experiments were conducted at lower temperature and even lower GHSV. By comparing results obtained from Conditions 3 and 4 shown in Table 1, low temperature operation results in higher selectivity to ethanol and lower methane formation. On Rh catalysts, methane formation is very sensitive to temperature change.

Figure 5:
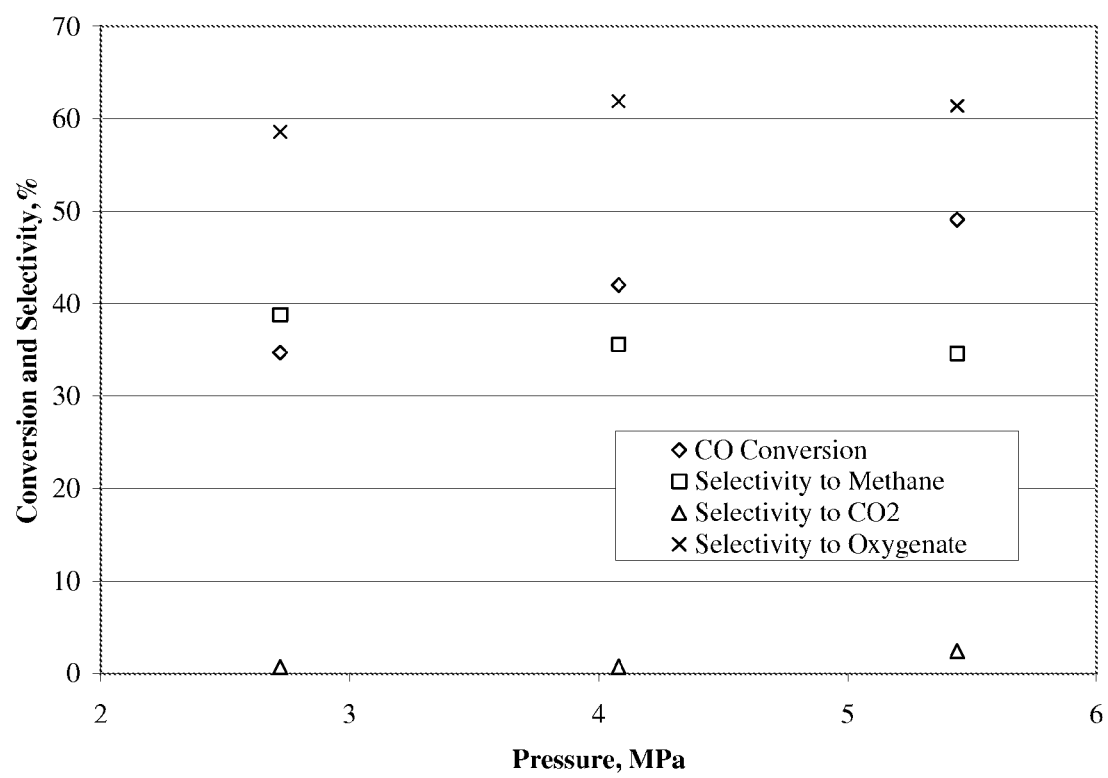
FIG. 5 Effect of reaction pressure on CO conversion and product selectivity over supported Rh catalysts (Rh—Mn—V/$SiO_2$ Catalyst, GHSV=1700 $h^{-1}$, $H_2$/CO=1:1).

The effect of pressure on the activity of Rh—Mn/$SiO_2$ catalyst was studied under constant temperature of 300° C. and GHSV=3750 $h^{-1}$, and results are summarized in Table 2. As the reaction proceeds from Condition 1 to Condition 2 wherein pressure is lowered from 5.4 to 3.8 MPa, conversion decreases whereas product selectivity remains essentially unchanged. This seems to indicate that when reaction is carried out at higher temperature of 300° C., the product selectivity is predominately controlled by reaction temperature rather than pressure, therefore changing pressure would not cause any noticeable impact on product selectivity. To further illustrate the effect of pressure on product selectivity, a reaction was carried out at relatively lower temperature of 270° C. The reactivity results at different reaction pressures are plotted in FIG. 5. At 270° C., an increase in CO conversion is observed with increased pressure. There is also an increase in selectivity to total oxygenates although it is not dramatic. However, in contrast to high temperature operation, a downward trend of methane selectivity is observed with increase in reaction pressure. Mechanistically, high pressure favors CO insertion into metal-$(CH_x)_{ad}$ surface species to form $C_2^+$ oxygenates, reducing the hydrogenation rate of $(CH_x)_{ad}$ for methane formation[4]. This implies that methane selectivity can be suppressed as long as the reactor is operated at temperature lower than about 270° C. The catalytic activity of Rh—Mn/$SiO_2$ catalyst was very steady, during 60 hours time on stream operation, no catalyst deactivation was observed.

TABLE 1

Influence Reaction Temperature on the Activity of Rh—Mn/$SiO_2$ Catalyst

| Conditions | 1 | 2 | 3 | 4 |
| --- | --- | --- | --- | --- |
| Temperature, ° C. | 280 | 300 | 280 | 265 |
| Pressure, MPa | 5.4 | 5.4 | 5.4 | 5.4 |
| GHSV, $h^{-1}$ | 3750 | 3750 | 1700 | 1700 |
| $H_2$/CO, mol/mol | 2 | 2 | 2 | 2 |
| CO Conversion | 24.6 | 40.5 | 38.7 | 25.1 |
| Selectivities, % | | | | |
| $CO_2$ | 0.0 | 3.4 | 1.3 | 0 |
| $CH_4$ | 38.4 | 48.1 | 40.2 | 34.2 |
| MeOH | 3.9 | 1.9 | 2.8 | 2.6 |
| EtOH | 56.1 | 44.5 | 53.9 | 61.4 |
| $C_2^+$HC and Oxy | 1.6 | 2.1 | 1.8 | 1.8 |

TABLE 2

Effect of Reaction Pressure and Feed Ratio on the Performance of Rh—Mn/$SiO_2$ Catalyst

| Conditions | 1 | 2 | 3 | 4 |
| --- | --- | --- | --- | --- |
| Temperature, ° C. | 300 | 300 | 300 | 300 |
| Pressure, MPa | 5.4 | 3.8 | 3.8 | 3.8 |
| GHSV, $h^{-1}$ | 3750 | 3750 | 3750 | 3750 |
| $H_2$/CO, mol/mol | 2 | 2 | 1 | 3 |
| CO Conversion, Mol % | 40.5 | 32.1 | 18.7 | 35.4 |
| Selectivities, % | | | | |
| $CO_2$ | 3.4 | 2.1 | 8.5 | 1.9 |
| $CH_4$ | 48.1 | 48.0 | 48.3 | 54.4 |
| MeOH | 1.9 | 3.2 | 2.1 | 1.9 |
| EtOH | 44.5 | 44.4 | 34.8 | 40.9 |
| $C_2^+$HC and Oxy | 2.1 | 2.3 | 6.3 | 0.9 |

Effect of $H_2$/CO Ratio on Product Selectivity

Figure 6:
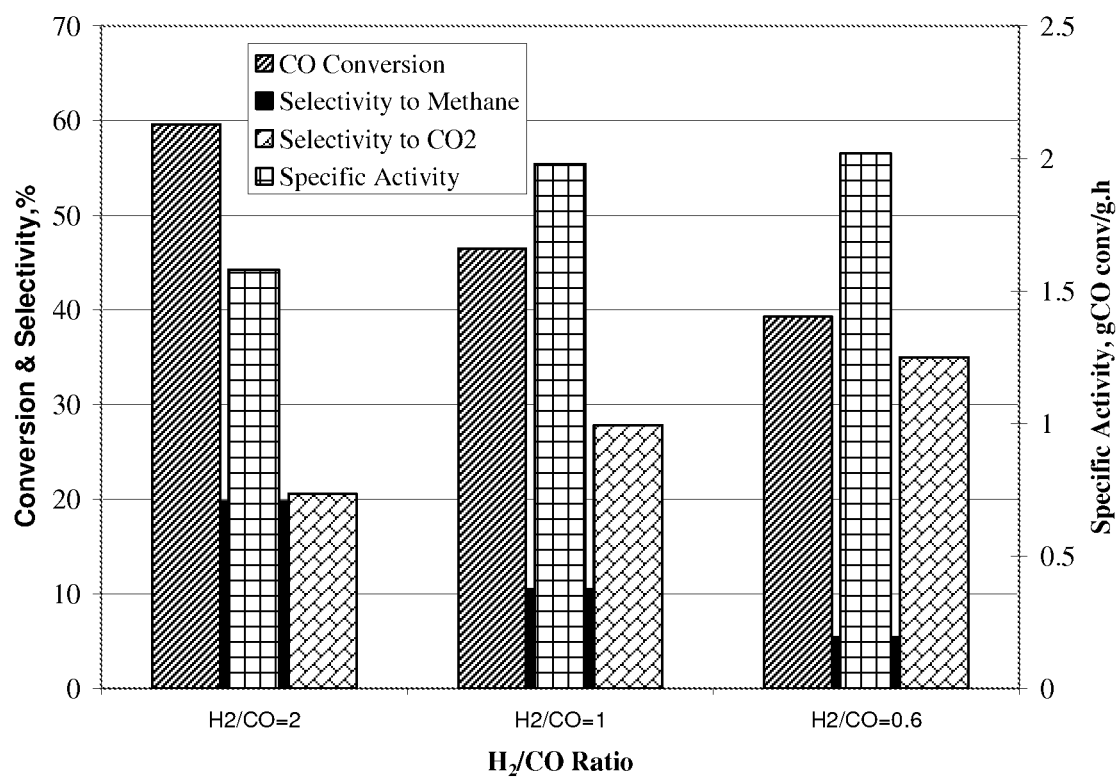
FIG. 6. Effect of $H_2$/CO ratio on conversion and product selectivity (Rh—Mn/$SiO_2$ catalyst, P=5.4 MPa, T=280° C., GHSV=3750 $h^{-1}$).
Figure 7:
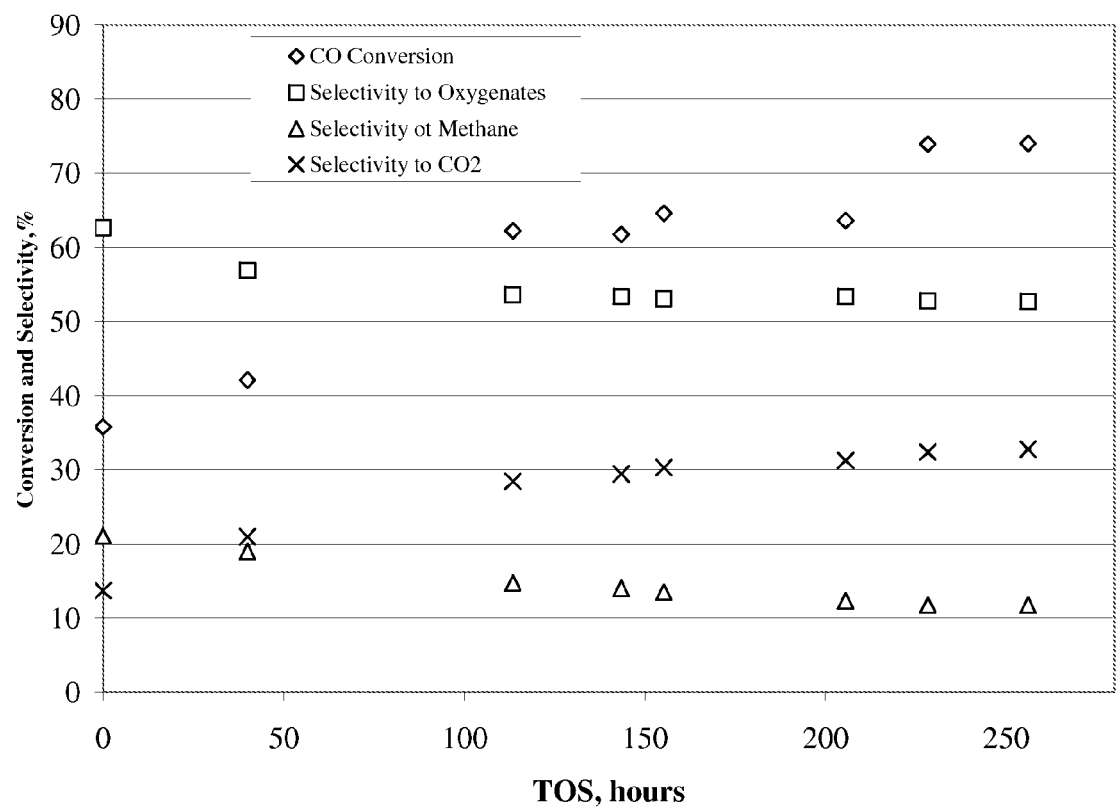
FIG. 7. Effect of RedOx treatment on the performance of hybrid catalyst system (CuZnAl and Rh—Mn/$SiO_2$ mixed at ratio of 1:2, P=5.4 MPa, GHSV=3750 $h^{-1}$, T=280° C.).

Table 2 illustrates the effect of varying $H_2$/CO ratio on the conversion and selectivity (Conditions 3-5). Experiments were carried out at 300° C., 3.8 MPa and GHSV=3750 $h^{-1}$, respectively. When $H_2$/CO ratio is reduced from 2 to 1 (Table 2, Conditions 2 to 3), CO conversion decreases sharply, and $CO_2$ selectivity increases, implying that water-gas-shift reaction becomes significant at lower $H_2$/CO ratio. Selectivity to ethanol is also reduced while undesired products $C_2^+$ hydrocarbons are increased. Changing from Condition 3 to Condition 4 where $H_2$/CO ratio is raised from 1 to 3, CO conversion increases and $CO_2$ selectivity decreases as anticipated. A slight increase in ethanol selectivity is observed. However, undesired product methane selectivity increases as well. It seems that on Rh—Mn/$SiO_2$ catalyst, high temperature and/or low pressure operation does not favor ethanol formation. Therefore, for testing with the Rh—Mn/$SiO_2$ catalyst, ethanol synthesis was limited to a narrow range of $H_2$/CO ratio. As a result, experiments were carried out to operate under high pressure but low temperature. The objective was to reveal the impact of $H_2$/CO on product selectivity under conditions favorable to ethanol formation. FIG. 6 presents the responses of CO conversion, methane selectivity, $CO_2$ selectivity as well as specific activity to the change in $H_2$/CO ratio. On decreasing $H_2$/CO ratio from 2 to 0.6, CO conversion decreases, selectivity to $CO_2$ increases while methane selectivity decreases considerably. The specific activity, in terms of mmol CO converted per gram of catalyst per hour, increases with the decrease in $H_2$/CO ratio. Because GHSV was kept constant during these experiments, although total CO conversion dropped, actual carbon conversion rate increased.

Effect of RedOx Cycle Treatment

The procedures employed to activate catalysts strongly influence activity of supported Rh catalysts. Different treatment procedures may result in different extent of Rh dispersion on the surface of an $SiO_2$ support. The influence of the dispersion on the activity and product selectivity of supported Rh catalyst has been the subject of several investigations[13-14]. The present investigation was undertaken in an effort to demonstrate the important catalyst activation procedures. One of the activation techniques adopted is called reduction-oxidation cycle, which is described in the experimental section. In industrial processes, e.g. gasoline reforming, this procedure has been adopted to activate supported noble metals to achieve high metal dispersion and stability.

Two catalysts, Rh—Mn/$SiO_2$ and Rh—Mn—V/$SiO_2$, were treated by a RedOx procedure and results are summarized in Tables 3 and 4. In comparison with regular hydrogen reduction treatment, RedOx treated Rh catalyst exhibits much higher initial conversion. During the initial stage (TOS less than 12 hours), change of selectivity to methane is within 1% for both catalysts. Although the RedOx treatment enhances overall conversion, it has no beneficial effect on methane formation. Consequently, under steady state operation (TOS=72 hours), CO conversion for RedOx treated catalysts is still 4% higher than regularly treated, while methane selectivity is increased by about 2% as well.

Figure 3:
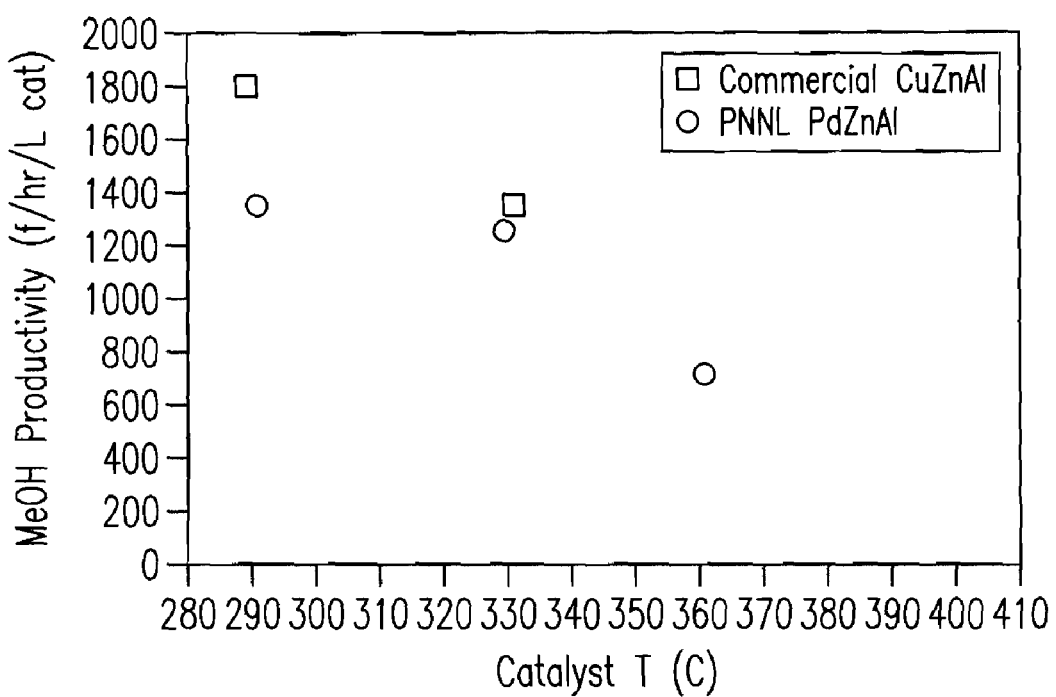
FIG. 3 Methanol synthesis comparing commercial CuZnAl catalyst to un-optimized PdZnAl catalyst. The conditions were: P=1170 psig, Feed=125 sccm, 70% $H_2$, 25% $CO_2$, 5% Ar.
Figure 4:
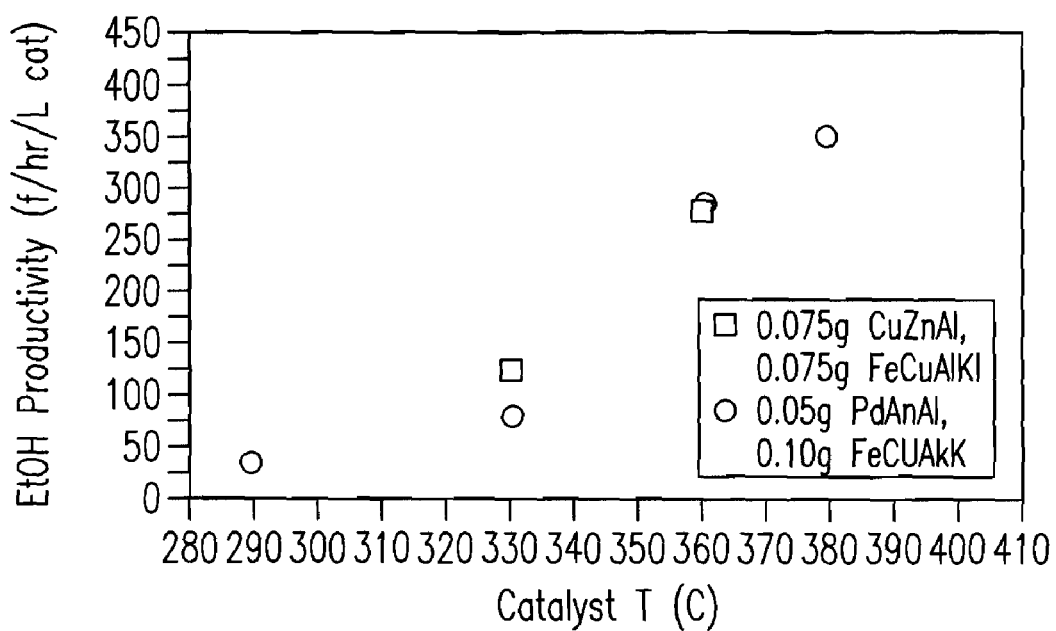
FIG. 4 Ethanol synthesis comparing a CuZnAl-Containing catalyst and a PdZnAl-containing catalyst under the same conditions as FIG. 3.

A hybrid catalyst system consisting of a Cu-based methanol synthesis catalyst and supported Rh catalyst was also treated by RedOx. The reason of using such a hybrid catalyst system was under the expectation that methanol precursors ($C_1$ species) produced on Cu catalyst might facilitate chain growth to yield $C_2$ oxygenate intermediates, favoring ethanol formation. After RedOx treatment, the time on stream performance of the hybrid catalyst system was monitored. Results are illustrated in FIG. 3. Surprisingly, after RedOx treatment, CO conversion continues to increase and does not level off until after 200 hours operation. Meanwhile, $CO_2$ selectivity exhibits an upward trend and levels off after 200 hours time on stream. The formation of $CO_2$ is expected which is mainly attributed to the well known water gas shift function of Cu-based catalyst. As the run proceeds, methane selectivity decreases from 20% to 10%. On the absolute basis, selectivity to methane on the hybrid catalyst is much lower than on supported Rh catalyst alone. During the entire 250 hours operation, variation of selectivity to oxygenates (containing mainly methanol and ethanol) is actually moderate, approaching a constant level at TOS=100 hours. The performance of such a catalyst system could be optimized by adjusting the ratio of the two catalysts.

Effect of Adding Alkali Metal

Potassium was added to Rh—Mn/$SiO_2$ catalyst in an attempt to inhibit methane formation and boost ethanol selectivity. It is well known that alkali metals promote chain growth on Cu based catalyst. Table 5 shows that adding Cs to methanol synthesis catalyst increases selectivity towards $C_2^+$ alcohols. However, it has not been demonstrated clearly in the literature whether alkali metal will promote $C_2^+$ alcohols on supported Rh catalysts. As shown in Table 5, when 3% K is added to Rh—Mn/$SiO_2$, CO conversion decreases. The negative impact of adding K or other alkali metals on CO conversion has been observed in many other catalyst systems used for syngas conversion. Compared with baseline Rh—Mn/$SiO_2$ catalyst, the addition of K results in significantly decreased methane selectivity. Although combined selectivity to methanol and ethanol increases as a result of decrease in methane selectivity, selectivity to ethanol alone decreases. The net gain is the methanol yield. The presence of K doesn't seem to promote chain growth on supported Rh catalyst, which is different from the Cu-based catalyst. This is probably because the reaction pathways on Cu and Rh based catalyst systems are significantly different.

Performance of Structured Catalyst Under High Throughput

As described above, a structured catalyst was prepared and tested to compare with identical powdered catalyst. The structured catalyst was coated on highly heat conducting material, a thin FeCrAlY metallic felt. The structured catalyst is closely attached to reactor channel wall where active cooling can be effective. A control run (reference run) was conducted using identical Rh—Mn/$SiO_2$ catalyst in the powdered form, and operated in a microchannel reactor of the same geometry. As shown in Table 6, in Run EC-02 using the structured catalyst, reaction can be carried out at flow rates of at least GHSV=20,000 $h^{-1}$ to achieve the same conversion level as the control run (Run ET-32) operated at GHSV seven times slower. Due to the use of structured catalyst (that is, a catalyst having a large pore support) and active heat removal, reaction temperature and methane selectivity did not "run away" at high throughput.

TABLE 3

Effect of Reduction-Oxidation Cycle Treatment on the Performance of Rh—Mn/$SiO_2$

| | Regular Reduction | | RedOx Cycle Treatment | |
|---|---|---|---|---|
| | Initial Activity TOS = 12 hours | Steady State Activity TOS = 72 hours | Initial Activity TOS = 12 hours | Steady State Activity TOS = 72 ours |
| CO Conversion, mol % | 58.9 | 52.9 | 65.3 | 56.6 |
| Selectivity, % | 33.0 | 32.9 | 34.0 | 35.2 |
| $CH_4$ | 0.0 | 0.3 | 1.3 | 1.1 |
| $CO_2$ | 0.9 | 1.2 | 1.4 | 1.5 |
| $C_2^+$HC Alcohols and $C_2^+$Oxy | 66.1 | 65.6 | 63.4 | 62.1 |

GHSV = 1700 $h^{-1}$, P = 5.4 MPa, T = 270° C., $H_2$/CO = 2:1

TABLE 4

Effect of Reduction and Oxidation Cycle Treatment on the Performance of Rh—Mn—V/$SiO_2$

| | Regular Reduction | | RedOx Cycle Treatment | |
|---|---|---|---|---|
| | Initial Activity TOS = 12 hours | Steady State Activity TOS = 72 hours | Initial Activity TOS = 12 hours | Steady State Activity TOS = 72 hours |
| CO Conversion, mol % | 49.1 | 42.4 | 55.3 | 46.4 |
| Selectivity, % | 34.6 | 34.8 | 35.2 | 37.1 |
| $CH_4$ | 2.4 | 1.4 | 2.4 | 1.1 |
| $CO_2$ | 1.6 | 1.7 | 1.7 | 1.7 |
| $C_2^+$HC Alcohols and $C_2^+$Oxy | 61.4 | 62.1 | 60.7 | 60.1 |

GHSV = 1700 $h^{-1}$, P = 5.4 MPa, T = 270° C., $H_2$/CO = 2:1

TABLE 5

Performance Comparison of Different Alcohol Synthesis Catalysts

| | Rh—Mn/$SiO_2$ | Rh—Mn—K/$SiO_2$ | Cu—Zn—Al—Cs |
|---|---|---|---|
| CO Conversion, mol % | 24.6 | 15.6 | 35.2 |
| Selectivity, % | | | |
| $CH_4$ | 38.4 | 27.4 | 0.3 |
| $CO_2$ | 0.0 | 0.0 | 0 |
| MeOH | 3.9 | 27.8 | 56.8 |
| EtOH | 56.1 | 44.3 | 30.0 |
| Other HC and Oxygenates | 1.6 | 0.5 | 12.9 |

T = 280° C., P = 5.4 MPa, GHSV = 3750 $h^{-1}$, $H_2$/CO = 2:1

| Catalyst Performance Comparison | | |
|---|---|---|
| Reaction Conditions and Performance | Our Data (Table 5) | Literature data* |
| GHSV, h$^{-1}$ | 3750 | 180 |
| T, °C. | 280 | 200 |
| P, MPa | 5.4 MPa | 0.1 |
| Catalyst | Rh—Mn/SiO$_2$ | Rh$_2$MnO$_4$/SiO$_2$ |
| CO Conversion, % | 24.6 | 20.2 |
| Selectivity | | |
| CH$_4$ | 38.4 | 42.3 |
| CO$_2$ | 0 | 3.0 |
| MeOH | 3.9 | 2.0 |
| EtOH and C$_2$ Oxygenates | 56.1 | 20.4 |
| Other HCs | 1.6 | 32.3 |

*S. Ishiguro, S. Ito, K. Kunimori, Catalysis Today 45, 197-201, 1998 (Table 1)

As can be seen, the use of a microchannel reactor allows us to operate at high throughput to achieve high conversion and improved selectivity.

TABLE 6

Performance Comparison of Structured Rh—Mn/SiO$_2$ Catalyst with Identical Powdered Form in a MicroChannel Reactor

| | Run numbers | |
|---|---|---|
| | Run EC-02 | Run ET 32 |
| Catalyst Configuration | Rh—Mn/SiO$_2$ coated on FeCrAlY felt | Powdered Rh—Mn/SiO$_2$ |
| GHSV, h$^{-1}$ | 20,000 | 2700 |
| Conversion, mol % | 20.4 | 22.7 |
| Selectivity, % | | |
| CH$_4$ | 36.5 | 31.1 |
| CO$_2$ | 2.3 | 4.7 |
| C$_2$$^+$HCs | 3.2 | 1.7 |
| Alcohols and C$_2$$^+$Oxy | 58.0 | 62.4 |
| Specific Activity, mmolCO Converted/g · h | 46.0 | 26.8 |

H$_2$/CO = 1:1, T = 300° C.

We claim:

1. A method of synthesizing alcohols from CO or CO$_2$ comprising:
   flowing a reactant gas mixture comprising H$_2$ and CO or CO$_2$ into contact with a catalyst;
   wherein the catalyst comprises a Pd—Zn alloy dispersed on alumina; and
   forming an alcohol or alcohols.

2. The method of claim 1 wherein the alcohol or alcohols formed in the step of forming an alcohol or alcohols consists essentially of methanol.

3. The method of claim 1 wherein the catalyst further comprises a Fisher-Tropsch catalyst and wherein the alcohol or alcohols formed in the step of forming an alcohol or alcohols comprises higher alcohols that contain 2 or more carbon atoms.

4. The method of claim 3 wherein the alcohol or alcohols formed in the step of forming an alcohol or alcohols comprises a mixture of alcohols in which ethanol is the principle alcohol.

5. The method of claim 3 wherein the catalyst comprises the Pd—Zn alloy dispersed on alumina catalyst and a Fisher-Tropsch catalyst that are mixed together.

6. The method of claim 3 wherein the catalyst comprises a first section that consists essentially of the Pd—Zn alloy dispersed on alumina catalyst, and a second section that comprises the Fisher-Tropsch catalyst.

7. The method of claim 3 wherein said step of flowing is controlled so that the contact time is less than 1 second.

8. The method of claim 7 wherein the catalyst is disposed in a reaction channel having a width of 5 mm or less, and further wherein the temperature variation across the catalyst is 10° C. or less.

9. The method of claim 6 wherein the first section and the second section are disposed in a reaction channel having a width of 5 mm or less.

10. The method of claim 6 wherein the reactant gas mixture contacts the first section before contacting the second section.

11. The method of claim 1 wherein the catalyst comprises crystalline ZnO.

12. The method of claim 2 wherein the reactant gas mixture comprises CO, and CO reacts with H$_2$ to form methanol.

13. The method of claim 1 wherein the reactant gas mixture comprises CO and CO$_2$.

14. The method of claim 1 wherein the reactant gas mixture consists essentially of CO and H$_2$.

15. A method of synthesizing ethanol or higher alcohols from CO$_2$ comprising:
   flowing a reactant gas mixture comprising CO$_2$ and H$_2$ into contact with a catalyst;
   wherein the catalyst comprises: (a) Pd—Zn alloy dispersed on alumina and (b) a Fischer-Tropsch catalyst; and
   forming ethanol or higher alcohols.

16. A method of synthesizing an alcohol comprising:
   contacting hydrogen and CO over an alcohol catalyst in a microchannel;
   removing heat into a heat exchanger; and
   converting at least 20% of the CO into products with a selectivity to C$_2$$^+$ oxygenates of at least 30%.

17. The method of claim 16 comprising a selectivity to ethanol of at least 30%.

18. The method of claim 16 wherein the catalyst is disposed in a flow-by configuration in the microchannel.

19. The method of claim 16 wherein the catalyst comprises an alcohol synthesis catalyst and a Fischer-Tropsch catalyst.

20. The method of claim 19 wherein the alcohol synthesis catalyst and Fischer-Tropsch catalyst are mixed together.

21. The method of claim 19 wherein the alcohol synthesis catalyst and Fischer-Tropsch catalyst are sequentially arranged in the microchannel.

22. The method of claim 16 wherein the catalyst comprises Rh and Mn disposed on silica, titania, or zirconia.

23. The method of claim 22 wherein the catalyst is disposed on a large pore support and wherein the catalyst on the large pore support has a pore volume in which at least 20% of the pore volume is composed of pores in the size range of 0.1 to 300 microns.

24. The method of claim 16 wherein temperature is maintained at less than about 270° C.

25. The method of claim 22 wherein temperature is maintained at less than about 270° C.

26. The method of claim 16 wherein and comprising passing reactants through the microchannel at a gas hourly space velocity of at least 3000 h$^{-1}$ and converting at least 20% of the CO into products with a selectivity to C$_2$$^+$ oxygenates of at least 40%.

27. The method of claim 18 wherein and comprising passing reactants through the microchannel at a gas hourly space velocity of at least 3000 h$^{-1}$.

28. A method of synthesizing alcohols from CO or $CO_2$ comprising:

flowing a reactant gas mixture comprising $H_2$ and CO or $CO_2$ into contact with a catalyst;

wherein the catalyst comprises Pd and Zn dispersed on alumina; wherein the catalyst has been activated by reducing in the presence of hydrogen at a temperature of at least 350° C.; and forming an alcohol or alcohols.

29. The method of claim 27 wherein the catalyst comprises 2 to 10 weight % Pd; and wherein the catalyst comprises Pd and Zn in a Pd:Zn molar ratio of 0.1 to 0.5.

30. The method of claim 27 wherein the catalyst has been activated by reducing in the presence of hydrogen at a temperature in the range of 400° C. to 500° C.

31. A method of synthesizing alcohols from CO or $CO_2$ comprising:

flowing a reactant gas mixture comprising $H_2$ and CO or $CO_2$ into contact with a catalyst;

wherein the catalyst comprises Pd and Zn dispersed on alumina;

wherein the catalyst is disposed in a microchannel and wherein heat generated in the microchannel is transferred to an adjacent heat exchanger; and forming an alcohol or alcohols.

32. The method of claim 31 wherein the catalyst comprises 2 to 10 weight % Pd; and wherein the catalyst comprises Pd and Zn in a Pd:Zn molar ratio of 0.1 to 0.5.

\* \* \* \* \*